(12) United States Patent
Jeong et al.

(10) Patent No.: US 7,067,508 B2
(45) Date of Patent: Jun. 27, 2006

(54) DIAMINEDITHIOL DERIVATIVES AND RADIORHENIUM OR RADIOTECHNETIUM COMPLEX THEREOF; A LIVER CANCER-TREATING COMPOSITION COMPRISING THE RADIORHENIUM COMPLEX AND LIPIODOL; AND A KIT FOR PREPARATION OF THE LIVER CANCER-TREATING COMPOSITION

(75) Inventors: Jae Min Jeong, Seoul (KR); Young Ju Kim, Puchon-si (KR); Yun-Sang Lee, Seoul (KR); Dong Soo Lee, Seoul (KR); June-Key Chung, Seoul (KR); Myung Chul Lee, Seoul (KR)

(73) Assignee: Seoul National University Industry Foundation (KR)

( * ) Notice: Subject to any disclaimer, the term of this patent is extended or adjusted under 35 U.S.C. 154(b) by 151 days.

(21) Appl. No.: 10/469,198

(22) PCT Filed: Mar. 8, 2002

(86) PCT No.: PCT/KR02/00404

§ 371 (c)(1),
(2), (4) Date: Aug. 25, 2003

(87) PCT Pub. No.: WO02/074736

PCT Pub. Date: Sep. 26, 2002

(65) Prior Publication Data
US 2004/0087567 A1    May 6, 2004

(30) Foreign Application Priority Data
Mar. 19, 2001  (KR) ................................. 2001-13987

(51) Int. Cl.
*A01N 43/00* (2006.01)
*A61K 31/33* (2006.01)

(52) U.S. Cl. .......................... 514/183; 514/665; 514/9; 530/317; 540/467; 564/500

(58) Field of Classification Search ................ 514/183, 514/665, 9; 530/317; 540/467; 564/500
See application file for complete search history.

(56) References Cited

U.S. PATENT DOCUMENTS 5,095,111 A * 3/1992 Lever et al. ................. 540/544
5,196,515 A * 3/1993 Lever et al. ................. 530/363
5,496,533 A * 3/1996 Jackson et al. ............ 424/1.65

* cited by examiner

*Primary Examiner*—Johann Richter
*Assistant Examiner*—Chukwuma Nwaonicha
(74) *Attorney, Agent, or Firm*—Bachman & LaPointe, P.C.

(57) ABSTRACT

The present invention relates to a novel diaminedithiol derivative or a pharmaceutically acceptable salt thereof; radiorhenium or radiotechneticum complex thereof; a composition for treating liver cancer comprising the radiorhenium complex and lipiodol; and, a preparative kit of the composition for treating liver cancer.

In the composition according to the invention, the diaminedithiol derivative is a novel compound in which long chain alkyl groups were introduced to diaminedithiol, capable of forming a radiorhenium or radiotechnetium complex thereof with an ease and leading to stronger van der Waals bonds with lipiodol. As a result, the complex becomes more stable in a medium, lipiodol, whereby the composition of the invention exhibits a high accumulation rate in liver cancer tissue when injected via hepatic artery, thereby capable of achieving an efficient treatment of liver cancer.

13 Claims, No Drawings

DIAMINEDITHIOL DERIVATIVES AND RADIORHENIUM OR RADIOTECHNETIUM COMPLEX THEREOF; A LIVER CANCER-TREATING COMPOSITION COMPRISING THE RADIORHENIUM COMPLEX AND LIPIODOL; AND A KIT FOR PREPARATION OF THE LIVER CANCER-TREATING COMPOSITION

TECHNICAL FIELD

The present invention relates to a novel diaminedithiol derivative or a pharmaceutically acceptable salt thereof; a radiorhenium or radiotechnetium complex thereof; a composition for treating liver cancer comprising the radiorhenium complex and lipiodol; and a preparative kit of the composition for treating liver cancer.

BACKGROUND ART

Liver cancer especially affects oriental countries, including Korea at a high incidence and mortality rate. The liver cancer can be treated by surgical operation in an early stage, when metastasis of cancer cells has not occurred and their size is small. However, as the disease is progressed, the treatment by the surgical operation becomes ineffective. In this case, hepatic arterial embolization is generally used.

Normal liver tissue is supplied with blood and oxygen through both portal veins and arteries, particularly, for the blood the portal veins and arteries being responsible for 75% and 25%, respectively, of the total supply, and for the oxygen the portal veins and arteries being responsible for 50% and 50%, respectively, of the total supply. However, as for a cancerous tissue of the liver, the portal veins take 90% in supplying blood. Based on this fact, if embolic material embolizing to capillary vessel is injected to the hepatic artery of a liver cancer patient, the material is migrated mainly to the liver cancer tissue, causing embolization thereto. One example of the embolic materials is lipiodol.

Lipiodol is a lipid-soluble contrast medium obtained by iodination and esterification of poppy seed oil. Lipiodol has been employed as a contrast medium for imaging lymph nodes. It is easily able to cause capillary embolism due to 38 weight % iodine and high viscosity at room temperature. Therefore, injection of lipiodol to the hepatic artery of a patient with liver cancer results in lipiodol being concentrated into the liver cancer tissue. Using, such information, there were several attempts to treat liver cancer by injecting anticancer agent-assembled lipiodol to the liver cancer tissue.

A method by which lipiodol is labeled with a radioisotope and administered via a hepatic artery to treat liver cancer had been used. It was reported that when administered to patients with liver cancer, $^{131}$I-labelled lipiodol is accumulated in liver cancer tissue (M. Nakajo et al., Biodistribution and in vivo kinetics of iodine-131 lipiodol infused via the hepatic artery of patients with hepatic cancer, J. Nucl. Med., 29: 1066–1077, 1988). And, distribution in vivo of $^{90}$Y-labelled lipiodol was studied (S-J Wang et al., Preparation and biodistribution of yttrium-90 lipiodol in rats following hepatic arterial injection, Eur. J. Necl. Med., 22: 233–236, 1995). However, there are disadvantages in that I-131 is an isotope not suitable for the treatment, and Y-90 is costly and hard to be imaged, limiting the use thereof. Articles were published to report Re-188 labeling to overcome the above disadvantages (S-J Wang et al., Radiolabelling of lipiodol with generator-produced $^{188}$Re for hepatic tumor therapy, Appl. Radiat. Isot., 47: 267–271., 1996; S-J Wang et al., Biodistribution of rhenium-188 lipiodol infused via the hepatic artery of rats with hepatic tumors, Eur. J. Nucl. Med., 23:13–17, 1996). However, the methods presented by these articles need improvement since the labeling method is complicated and the labeling efficiency and its stability are low.

To improve the labeling method, diaminedithiol derivatives with alkyl chain have been developed (T W Jackson et al., Rhenium diamino dithiol complexes. III Lipophilic ligands for endotherapeutic radiopharmaceuticals. Aust. J. Chem. 53:983–987). They synthesized diaminedithiol derivatives with long alkyl chain of $C_1$–$C_{14}$ and labeled them with radiorhenium. What they found was that only diaminedithiol derivatives with alkyl chain of $C_1$–$C_{10}$ showed enough stability for treatment of liver cancer. They found that diaminedithiol derivatives with alkyl chain longer than $C_{10}$ were not stable. Actually, they reported that the yield of complexing rhenium and diaminedithiol containing $C_{10}$ alkyl chain was so poor that they failed to get enough amount of complex for analysis. It would have been even more difficult for them to obtain rhenium complex with diaminedithiol containing longer alkyl chain in their experiment. That is why they gave up diaminedithiol containing alkyl chain longer than $C_{10}$. They claimed diaminedithiol derivatives with alkyl chain of $C_1$–$C_{10}$ for treatment of liver cancer in U.S. Pat. No. 5,496,533. However in our experiment, diaminedithiol containing alkyl chain longer than $C_{10}$ could make stable lipophilic complex with $^{183}$Re. Furthermore, we found that diaminedithiol derivatives with alkyl chain shorter than $C_{13}$, which includes the compounds in U.S. Pat. No. 5,496.533, were not lipophilic enough to be retained in the tissue, which would result in rapid clearance from cancer tissue. We have proved that diaminedithiol derivatives should have alkyl chain longer than $C_{14}$, and that is our major claim in this patent.

Meanwhile, diaminedithiol has a structure represented in Formula 1 below. It was synthesized and known to make stable lipophilic complex with technetium or rhenium (H F Kung, et al. Synthesis and biodistribution of neutral lipid-soluble Tc-99 m complexes that cross the blood-brain barrier. J. Nucl. Med. 25:326–332, 1984). Davison et al described a variety of complexes of substituted anionic diaminedithiol with Tc-99 m as an agent for imaging kidney, which was published on Mar. 27, 1985 in Europe Pat. Appln. No. 135,160.

[Formula 1]

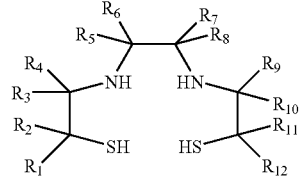

wherein, $R_1$ to $R_{12}$ are independently hydrogen, alkyl having $C_1$ to $C_3$, or —COOR (in which R is —$CH_3$, —$C_2H_5$ or —$C_3H_7$); provided that among substituents $R_1$ to $R_{12}$, only $R_3$, $R_5$, and $R_7$ to $R_{10}$ may be —COOR.

A kit comprising a neutral lipid-soluble ester-substituted is diaminedithiol is disclosed in Korean Pat. Laid-open No. 92-2107. According to the reference, using a method by which thiazolidine is dimerized via reduction to prepare a N,N'-1,2-ethylenebis-L-cysteine derivative and ester, thereof (Blondeau et al., Can. J. chem., 45:46, 1967). ligand is synthesized and labeled with Tc-99 m to form a neutral lipid-soluble complex, being directed to imaging blood flow in the brain.

In U.S. Pat. No. 5,980,860 published on Nov. 9, 1999, it is described that diaminedithiol derivatives are synthesized by introducing tropane group to use as a radiopharmaceuticals for imaging dopamine transporter.

DISCLOSURE OF THE INVENTION

Therefore, the present invention has been made in view of the above problems, and it is an object of the present invention to provide a novel diaminedithiol derivative and pharmaceutically acceptable salts thereof.

It is a further object of the present invention to provide a complex of diaminedithiol derivative-radiorhenium or a complex of diaminedithiol derivative-radiotechnetium.

It is yet another object of the present invention to provide a composition for treating liver cancer comprising a complex of novel diaminedithiol derivative-radiorhenium, which is able to be prepared easily and is stable after preparation, characterized by its high and durable accumulation in liver cancer tissue, thereby being capable of efficiently treating liver cancer without any side effect.

In particular, it is an important object of the invention to provide a more effective composition for treating liver cancer, which compensates for a shortcoming that a complex of diaminedithiol-rhenium fails to be retained in a tissue for a long time.

BEST MODE FOR CARRYING OUT THE INVENTION

The present invention relates to a novel diaminedithiol derivative having long chain alkyl groups, represented in Formula 2 below (hereinafter, referred to as diaminedithiol derivative) or a pharmaceutically acceptable salt thereof; a radiorhenium or radiotechnetium complex thereof; a composition for treating liver cancer comprising the radiorhenium complex and lipiodol; and, a preparative kit of the composition for treating liver cancer.

The diaminedithiol derivative of the present invention, represented in Formula 2 below, and pharmaceutically acceptable salts thereof are novel compounds and form complexes with radiorhenium or radiotechnetium. The complex compound of diaminedithiol derivative-radiorhenium creates stronger Van der Waals bonds by the introduction of lone chain alkyl groups. As a result, the complex becomes more stable in the medium, lipiodol. Moreover, a technetium complex of diaminedithiol derivative may be an agent for imaging blood flow in the lung via intravenous injection after being dissolved in lipiodol or oil which is a liquid at room temperature.

[Formula 2]

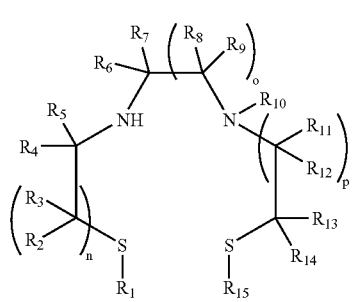

wherein:

$R_2$, $R_3$, $R_8$ to $R_{14}$ are independently hydrogen or lower alkyl having $C_1$ to $C_5$; $R_4$ and $R_5$ are independently hydrogen or lower alkyl having $C_1$ to $C_5$ or they form oxo (=O) group; $R_6$ and $R_7$ are independently hydrogen or lower alkyl having $C_1$ to $C_5$ or they form oxo (=O) group, in which at least one of $R_2$ to $R_{14}$ is higher alkyl having $C_{15}$ to $C_{24}$ and $R_4$ to $R_7$ don't form two oxo (=O) groups at the same time:

$R_1$ and $R_{15}$ are independently hydrogen or thiol protecting group such as benzoyl, acetamidomethyl, diphenylmethyl, ethylaminocarbonyl, t-butyl, trityl and acetyl, or $R_1$ and $R_{15}$ together form a S—S bond; and, n, o, p are independently 1 or 2.

In the above, if $R_1$ and $R_{15}$ are thiol protective groups, they should be removed immediately before or when being labelled to form a thiol group.

In he above Formula 2, as for the preparation of a composition for treating liver cancer, diaminedithiol derivatives in which $R_{10}$ is higher alkyl having $C_{15}$ to $C_{24}$, or pharmaceutically acceptable salts hereof are preferable. More preferably, diaminedithiol derivatives in which $R_{10}$ is higher alkyl having $C_{15}$ to $C_{20}$, or pharmaceutically acceptable salts thereof may be employed. In addition, it may be expected that a diaminedithiol derivative in which $R_{10}$ is linear alkyl without a branch, or pharmaceutically acceptable salts thereof offers more desirable effects.

In the above Formula 2, diaminedithiol derivatives in which n, o and p are all together 1 or pharmaceutically acceptable salts thereof may be preferably employed for the preparation of a composition for treating liver cancer.

Furthermore, diaminedithiol derivatives in which all the above conditions are met; $R_2$, $R_3$, $R_{13}$ and $R_{14}$ are all together methyl; $R_1$, $R_4$, $R_5$, $R_6$, $R_7$, $R_8$, $R_9$, $R_{11}$, $R_{12}$ and $R_{15}$ are all together hydrogen, or pharmaceutically acceptable salts thereof may be most preferably employed.

Meanwhile, in the above Formula 2, $R_4$ and $R_5$ or $R_6$ and $R_7$, can be independently oxo (=O) group. If the compound has two or more oxo (=O) groups, its suitability decreases as an ingredient for a composition for treating liver cancer. Therefore, the compound which has only one oxo (=O) group may be preferably employed for the preparation of a composition for treating liver cancer.

A composition for treating liver cancer of the invention comprises a complex of diaminedithiol derivative-radiorhenium and lipiodol. A method for preparing the composition comprises the steps of reacting a diaminedithiol derivative, a reducing agent and an additive with radiorhenium or radiotechnetium to form a complex and dissolving the complex in lipiodol.

Radiorhenium used herein for forming a complex with a diaminedithiol derivative is either $^{186}$Re or $^{188}$Re and radiotechnetium used is $^{99m}$Tc. A reducing agent is used to reduce radiorhenium or radiotechnetium so as to allow binding with diaminedithiol. The reducing agent may be, for example, tin chloride, vitamin C, iron chloride, dithionite or sodium sulfite, and especially, tin chloride is preferable. Additives may be added for preventing the formation of byproducts upon radioisotope labeling and increasing the labeling efficiency as well as for improving a quality including chemical and physical stabilities of the labeling. The additives may be, for example, tartaric acid, gluconic acid, glucoheptonic acid, lactic acid, MDP, lactose, EDTA, gentisic acid, and especially, tartaric acid is preferable.

In view of the course of labeling with radiorhenium or radiotechnetium, when materials and methods disclosed in the prior art (S-J Wang et al., Radiolabelling of lipiodol with generator-produced $^{188}$Re for hepatic tumor therapy, Appl.

Radiat. Isot., 47: 267–271, 1996) are employed for labeling, ammonium carbonate solution is boiled, acetic acid is added, followed by evaporation under a nitrogen gas atmosphere, taking over 5 hours to get through the serial steps. On the other hand, labeling the diaminedithiol derivative used in this invention with radiorhenium is achieved within 1 hour and the complex formed has an excellent stability.

Lipiodol as a component for the composition of the invention, as described in the above section, is a lipid-soluble material. It was found by Nakamura et al in 1983 that lipidol is selectively accumulated in the liver cancer tissues. The composition according to the invention comprises lipiodol as a medium, being capable of accumulating a complex of diaminedithiol-radiorhenium or a complex of diaminedithiol-radiotechnetium, an active ingredient, in liver cancer tissues or lung tissues. The lipiodol content in the composition is any amount which can dissolve a complex of diaminedithiol-radiorhenium formed. Preferably, lipiodol may be employed in amount of 0.5 ml to 50 ml, relative to 1 mg of a diaminedithiol derivative.

As an active ingredient of the invention, a complex of diaminedithiol-radiorhenium is so highly lipid-soluble that it is well dissolved in lipiodol, an oil-based X-ray contrast medium. Thus, when lipiodol is used as a medium, injection of the complex of diaminedithiol-radiorhenium together with lipiodol through the hepatic artery causes embolization in capillary vessels of the liver cancer tissue, thereby the active ingredient being accumulated. A complex of diaminedithiol-radiorhenium is highly lipid-soluble so it remains dissolved in lipiodol and does not diffuse into surrounding tissues, whereby the complex is retained in the cancer tissue as long as lipiodol is held, finally achieving a selective radiation effect, thereby capable of selectively removing tumor cells.

With regard to the concrete method of preparing a composition for treating liver cancer of the invention, first, a diaminedithiol derivative reacts with radiorhenium in the presence of a reducing agent and an additive to form a complex. To the complex in aqueous solution is added lipiodol and the solution is mixed well. The lipid-soluble complex is mixed with lipiodol and the mixture is centrifuged, separating into two phases. The lower phase comprising lipiodol is taken out using a syringe to obtain a composition for treating liver cancer according to the invention.

Another embodiment of the invention is a preparative kit of the above composition for treating liver cancer comprising a first container containing a lyophilized diaminedithiol derivative, a reducing agent and an additive; and a second container containing lipiodol which can be subjected to a direct centrifugation. The reducing agent and additive are defined as above. Meanwhile, radiorhenium may be supplied from other sources immediately before use.

Further, in the above preparative kit of the composition for treating liver cancer, lipiodol may be supplied from other sources, thus, the kit is characterized by comprising a first container containing a lyophilized diaminedithiol derivative, a reducing agent and an additive, whereby a preparative kit comprising a complex of diaminedithiol derivative-radiorhenium in the composition for treating liver cancer is also available.

Hereinafter, the present invention will be described in detail, in conjunction with various examples. These examples are provided only for illustrative purposes, and the present invention is not to be construed as being limited to those examples.

EXAMPLE 1

Preparation of 5-octyl-3,3,10,10-tetramethyl-1,2-dithia-5,8-diazacyclodecane (OTDD)

Partial Synthesis A: Preparation of 3,3,10,10-tetramethyl-1,2-dithia-5,8-diazacyclodecane (TDD)

29 g of 2–2'-dithio-bis(2-methylpropanal) was dissolved in a solution of 50 mg tosic acid in 280 ml benzene and added dropwise with 12.6 g of 2-methyl-1,2-diaminopropane, while mixing well. The reaction mixture was refluxed for 2 hrs to remove water. Solvent was removed under reduced pressure. The residue was dissolved in petroleum ether with a low boiling point. Then, activated charcoal was added and the mixture was then filtered. The filtrate was concentrated until precipitates began to be formed. The crystals were filtered, collected and washed with cold petroleum ether to obtain light yellow crystals. The crystals thus obtained were dissolved in ethanol and added with sodium cyanoborohydride of the same equivalent while stirring gently. The solution was adjusted to pH 5.0 by adding glacial acetic acid. The reaction was let to stand at room temperature for 2 hrs. Then, the reaction solution was heated to 60° C. and stirred for 6 hrs. At this time, glacial acetic acid was added to maintain pH 5.0 until the reaction was completed. After 6 hrs, saturated ammonium chloride solution (10 ml) was added, and the solution was stirred for an additional 20 min. Solvent was removed under reduced pressure. The residue thereby obtained was added with 1 M sodium hydroxide solution (5 ml) and dissolved. The resulting solution was extracted with chloroform (20 ml). The organic phase was washed with saturated sodium chloride solution and dried over anhydrous sodium sulfate. After removing solvent from this product under reduced pressure, a light brownish liquid was obtained.

TLC (silica gel/diethylether:n-hexane:n-propylamine=7:3:1):$R_f$=0.3

$^1$H-NMR(CDCl$_3$): 1.24(s, 6H), 1.36(s, 6H), 2.34(s, 2H), 2.55~2.59(d, 2H, J=12.0 Hz), 2.80(s, 4H), 2.98~3.02(d, 2H, J=12.0 Hz). MS(EI m/z) 234.2(M+, 12%), 130.2(100%).

Partial Synthesis B: Preparation of OTDD

TDD (3.0 g, 12.8 mmol) prepared in the above section A was dissolved in acetonitrile (30 ml) and stirred at room temperature for 1 hr. To the solution was added 1-iodooctane (2.24 ml, 12.2 mmol) and the solution was stirred at room temperature for 12 hrs. The reaction mixture was filtered and the filtrate was concentrated by distilling under reduced pressure. The concentrate was separated by means of a preparative thin layer chromatography (diethylether:n-hexane:n-propylamine=30:30:1) to obtain a light yellow oil (1.11 g, 3.20 mmol, 26.3%).

TLC (silica gel/diethylether:n-hexane:n-propylamine=7:3:1):$R_f$=0.7

$^1$H-NMR(CDCl$_3$): 0.88(t, 3H, J=6.8Hz), 1.21–1.38(m, 24H), 1.52(t, 2H, J=7.1Hz), 1.83(bs, 1H), 2.47–2.86(m, 8H). MS(EI m/z) 346.4(M+, 17%), 204.1(100%)

EXAMPLE 2

Preparation of 5-dodecyl-3,3,10,10-tetramethyl-1,2-dithia-5,8-diazacyclodecane (DTDD)

TDD (3.0 g, 12.8 mmol) prepared in the above section A of Example 1 was dissolved in acetonitrile (30 ml). Potassium carbonate (17.7 g, 128 mmol) was added and the solution was stirred at room temperature for 1 hr. To the solution was added 1-iododecane (3.06 ml, 12.2 mmol) and the solution was stirred at room temperature for 12 hrs. The reaction mixture was filtered and the filtrate was concentrated by distilling under reduced pressure. The concentrate was separated by means of a preparative thin layer chromatography (diethylether:n-hexane:n-propylamine=30:30:1) to obtain a light yellow oil (1.49 g, 3.70 mmol, 30.3%).

TLC (silica gel/diethylether:n-hexane:n-propylamine=7:3:1):$R_f$=0.7

$^1$H-NMR(CDCl$_3$): 0.88(t, 3H, J=6.8Hz), 1.22–1.35(m, 32H), 1.52(t, 2H, J=7.1Hz), 1.96(bs, 1H), 2.55–2.87(m, 8H). MS(EI m/z) 402.4(M+, 14%), 204.1(100%)

EXAMPLE 3

Preparation of 5-hexadecyl-3,3,10,10-tetramethyl-1,2-dithia-5,8-diazacyclodecane (HTDD)

TDD (1.75 g, 7.47 mmol) prepared in the above A of Example 1 was dissolved in acetonitrile (20 ml). Potassium carbonate (10.3 g, 74.7 mmol) was added and the solution was stirred at room temperature for 1 hr. To the solution was added 1-iodohexadecane (2.35 ml, 7.1 ml) and the solution was stirred at room temperature for 12 hrs. The reaction mixture was filtered and the filtrate was concentrated by distilling under reduced pressure. The concentrate was separated by means of a preparative thin layer chromatography (diethylether:n-hexane:n-propylamine=30:30:1) to obtain a light yellow oil (0.66 g, 1.40 mmol, 19.2%).

TLC (silica gel/diethylether:n-hexane:n-propylamine=7:3:1):$R_f$=0.7

$^1$H-NMR(CDCl$_3$): 0.88(t, 3H, J=6.8Hz), 1.23–1.35(m, 40H), 1.52(t, 2H, J=7.1Hz), 2.05(bs, 1H), 2.55–2.86(m, 8H)

EXAMPLE 4

Preparation of N1-(2-(tritylsulfanyl)ethyl)-2-hexadecyl-(2-(tritylsulfanyl)ethyl)amino)acetamide Partial Synthesis A: Preparation of 2-(tritylsulfanyl)-1-ethaneamine 2-Aminoethanethiol hydrochloride (1.0 g, 8.6 mmol) was dissolved in acetic trifluoride (10 ml) and added with triphenylmethanol (2.32 g, 8.6 mmol). The resulting solution was stirred at room temperature for 1 hr and concentrated by distilling under reduced pressure. The filtrate was diluted with ethyl acetate (50 ml) and washed with 3 M sodium hydroxide aqueous solution, water, saturated sodium bicarbonate aqueous solution, saturated sodium chloride aqueous solution in sequence. The organic phase was dried over anhydrous sodium sulfate and distilled under reduced pressure to obtain a white solid of 2-(tritylsulfanyl)-1-ethaneamine (2.32 g, 7.3 mmol, 85.2%).

mp: 142–143° C.

TLC (silica gel/ethyl acetate:n-hexane=1:1):$R_f$=0.1

$^1$H-NMR(CDCl$_3$): 2.33(t, 2H), 2.57(t, 2H). 4.76(bs, 2H), 7.21–7.31 (m9H), 7.42–7.45(m, 6H)

Partial Synthesis B: Preparation of N1-(2-(tritylsulfanyl)ethyl)-2-bromoacetamide 2-(tritylsulfanyl)-1-ethaneamine (0.5 g, 1.6 mmol) was dissolved in methylene chloride (10 ml) and added with triethylamine (0.22 ml, 1.6 mmol). To the solution, bromoacetylbromide (0.14 ml, 1.6 mmol) in methylene chloride (1 ml) was added dropwise. The resulting solution was stirred at room temperature for 15 min and added with water (30 ml). The organic phase was washed with 1 M hydrogen chloride, water, saturated sodium bicarbonate aqueous solution, and saturated sodium chloride aqueous solution in sequence. The organic phase was dried over anhydrous sodium sulfate and distilled under reduced pressure to obtain a white solid of N1-(2(tritylsulfanyl)ethyl)-2-bromoacetamide (0.67 g, 1.51 mmol, 94.2%).

mp: 223–224° C.

TLC (silica gel/ethyl acetate:n-hexane=3:1):$R_f$=0.45

$^1$H-NMR(CDCl$_3$): 2.43(t, 2H), 3.11(q, 2H), 6.57(s, 1H), 7.21–7.31(m, 9H), 7.42–7.45(m, 6H)

Partial Synthesis C: Preparation of N1-(2-(tritylsulfanyl)ethyl)-2-((2(tritylsulfanyl)ethyl)amino)acetamide N1-(2-(tritylsulfanyl)ethyl)-2-bromoacetamide (0.5 g, 1.1 mmol) was dissolved in methylene chloride (5 ml) and added with triethylamine (0.23 ml, 1.6 mmol). To the solution was added with 2-(tritylsulfanyl)-1-ethaneamine (0.4 g, 1.1 mmol) and the resulting solution was stirred at room temperature for 16 hrs. The organic phase was dried over anhydrous sodium sulfate. The solvent was removed under reduced pressure. The product was purified by means of column chromatography to obtain a white solid of N1-(2 (tritylsulfanyl(ethyl)-2-((2-tritylsulfanyl)ethyl) amino)acetamide (0.4 g, 0.6 mmol, 55.3%).

mp: 88–92° C.

TLC (silica gel/ethyl acetate:n-hexane=2:1):$R_f$=0.4

$^1$H-NMR(CDCl$_3$): 2.37(q, 4H), 2.46(t, 2H), 3.04(s, 2H), 3.08(q, 2H), 7.18–7.30(m, 18H), 7.39–7.44(m, 12H)

Partial Synthesis D: Preparation of N1-(2-(tritylsulfanyl)ethyl)-2-(hexadecyl(2-(tritylsulfanyl)ethyl)amino)acetamide N1-(2-(tritylsulfanyl)ethyl)-2-((2-(tritylsulfanyl)ethyl) amino)acetamide (0.1 g, 0.15 mmol) was dissolved in anhydrous acetonitrile (5 ml) and added potassium carbonate (9243 mg, 1.5 mmol). The resulting solution was stirred at room temperature for 1 hr and added with 1-iodohexane (32 μl, 0.097 ml) in chloroform (1.5 ml). The solution was stirred at 45° C. for 12 hrs. Solvent was removed under reduced pressure. After adding chloroform (10 ml), the solution was filtered and the filtrate was concentrated and purified by means of column chromatography to obtain a yellow solid of N1-(2-(tritylsulfanyl)ethyl)-2-hexadecyl(2-(tritylsulfanyl)ethyl)amino)acetamide (44 mg, 32.5%).

mp: 188–193° C.

TLC (silica gel/ethyl acetate:n-hexane=2:1):$R_f$=0.8

$^1$H-NMR(CDCl$_3$): 0.88(t, 2H), 1.23–1.35(m, 30H), 2.37 (q, 4H), 2.46(t, 2H), 3.04(s, 2H), 3.08(q, 2H), 7.18–7.30(m, 18H), 7.39–7.44(m, 12H)

EXAMPLE 5

Preparation of $^{188}$Re-OTDD

OTDD (0.5 mg, 1.45 μmol) and glucoheptonic acid (200 mg, 960 μmol) were mixed with 0.1 M hydrogen chloride solution (0.125 ml) and added with stannous chloride dihydrate (10 mg, 44 μmol) in 0.0132 M hydrogen chloride aqueous solution (1 ml). To the mixed solution was added $^{188}$Re-perrhenic acid solution (20 mCi, 2.5 ml) and the resulting solution was incubated in a water bath at 100° C. for 1 hr. The product was obtained at 41.5% yield.

ITLC-SG (ethyl acetate): $R_f$=0.9

EXAMPLE 6

Preparation of $^{188}$Re-DTDD

DTDD (0.5 mg, 1.24 μmol) was dissolved in ethanol (0.1 ml) and added with stannum powder (5 mg, 42 μmol) dissolved in 10.2 M HCl aqueous solution (50 μl). To the mixed solution was added a solution (1 ml) of glucoheptonic acid (200 mg, 960 μmol) and then, $^{188}$Re-perrhenic acid aqueous solution (20 mCi, 3 ml) was added. The resulting solution was incubated in a water bath at 100° C. for 1 hr. The product was obtained at 23.3% yield.

ITLC-SG (ethyl acetate): $R_f$=0.9

EXAMPLE 7

Preparation of $^{188}$Re-HTDD

HTDD (0.5 mg, 1.09 μmol) was dissolved in ethanol (0.1 ml) and added with stannum powder (5 mg, 42 μmol) dissolved in 10.2 M HCl aqueous solution (50 μl). To the mixed solution was added an aqueous solution (1 ml) of glucoheptonic acid (200 mg, 960 μmol) and then, added $^{188}$Re-perrhenic acid aqueous solution (20 mCi, 3 ml). The resulting solution was incubated in a water bath at 100° C. for 1 hr. The product was obtained at 14.3% yield.

ITLC-SG (ethyl acetate): $R_f$=0.9

EXAMPLE 8

Preparation of $^{188}$Re-Labelled Compound in Lipiodol Solution

To the $^{188}$Re-labelled reaction mixture prepared in the foregoing Examples 4 to 6, lipiodol (5 ml) was added, mixed well and the solution was centrifuged at 3000 rpm for 10 min. The supernatant was removed and 2 ml saline was added. After mixing well, the resulting solution was centrifuged again at 3000 rpm for 10 min and the supernatant was removed to recover a lower phase of lipiodol.

EXPERIMENTAL EXAMPLE 1

Observation of Increased Accumulation and Retention of $^{188}$Re-Labelled Compounds in Animal Tissues Mice (ICR) were administered with an injection of $^{188}$Re-labelled compound in lipiodol solution which was prepared in the Example 7 via the tail vein. Radioactivity distributed in tissues and weight of each tissue were measured to calculate the percentage of radioactivity per gram of unit tissue relative to total radioactivity administered.

As radiation accumulation mechanism in the lung and the liver cancer are similar, it is convenient to detect the level of radiation accumulating in the lung of a mouse suffering from liver cancer. As found in Tables 1 to 4, compounds with a long side chain (Tables 2 to 4) more readily accumulated in the lung, and the clearance rate is slower than for compounds without a long side chain (Table 1). Therefore, it can be inferred that a radiorhenium complex of a diaminedithiol derivative having a long side chain is effective for treating liver cancer.

TABLE 1

Biodistribution of the solution of $^{188}$Re-TDD in lipiodol in mice

| | Time post-injection | | |
|---|---|---|---|
| Specimen | 10 min. 4 mice | 1 hr 4 mice | 24 hr 3 mice |
| Blood | 4.4 ± 0.4 | 3.0 ± 0.7 | 0.6 ± 0.1 |
| Muscle | 4.1 ± 0.9 | 0.9 ± 0.3 | 0.2 ± 0.2 |
| Fat | 6.4 ± 0.6 | 2.5 ± 0.2 | 0.2 ± 0.0 |
| Heart | 9.8 ± 0.7 | 1.9 ± 0.2 | 0.5 ± 0.1 |
| Lung | 84.3 ± 25.8 | 15.7 ± 4.6 | 3.1 ± 0.2 |
| Liver | 25.2 ± 4.1 | 22.9 ± 3.8 | 3.6 ± 0.7 |
| Spleen | 3.5 ± 0.5 | 1.7 ± 0.2 | 0.4 ± 0.1 |
| Stomach | 3.6 ± 0.6 | 10.7 ± 1.3 | 3.2 ± 2.3 |
| Small intestine | 6.9 ± 1.6 | 22.3 ± 4.6 | 25.7 ± 12.8 |
| Kidney | 13.5 ± 2.5 | 6.2 ± 2.5 | 0.8 ± 0.1 |

TABLE 2

Biodistribution of the solution of $^{188}$Re-OTDD in lipiodol in mice

| | Time post-Injection | | | | |
|---|---|---|---|---|---|
| Specimen | 10 min 3 mice | 30 min 3 mice | 1 hr 4 mice | 3 hr 3 mice | 24 hr 3 mice |
| Blood | 5.2 ± 1.8 | 3.8 ± 0.4 | 3.1 ± 0.5 | 2.8 ± 0.3 | 0.6 ± 0.0 |
| Muscle | 1.5 ± 0.2 | 1.2 ± 0.2 | 0.9 ± 0.2 | 0.5 ± 0.1 | 0.2 ± 0.0 |
| Fat | 3.6 ± 0.7 | 2.2 ± 0.2 | 1.6 ± 0.4 | 1.3 ± 0.4 | 0.4 ± 0.1 |
| Heart | 6.3 ± 1.7 | 4.4 ± 0.3 | 2.7 ± 1.0 | 1.9 ± 0.4 | 0.7 ± 0.1 |
| Lung | 138.4 ± 19.8 | 97.4 ± 20.7 | 87.0 ± 13.2 | 61.6 ± 10.0 | 22.8 ± 3.3 |
| Liver | 15.1 ± 2.4 | 21.6 ± 4.9 | 20.1 ± 3.3 | 19.7 ± 6.7 | 7.3 ± 1.5 |
| Spleen | 2.6 ± 0.3 | 2.3 ± 0.1 | 1.9 ± 0.6 | 1.8 ± 0.3 | 2.0 ± 2.0 |
| Stomach | 3.5 ± 1.3 | 12.9 ± 6.6 | 11.1 ± 3.1 | 15.5 ± 6.6 | 3.6 ± 1.8 |
| Small intestine | 3.6 ± 0.3 | 8.0 ± 2.0 | 13.0 ± 3.7 | 23.4 ± 0.3 | 19.8 ± 12.0 |
| Kidney | 8.0 ± 1.2 | 6.6 ± 0.3 | 5.6 ± 0.9 | 4.0 ± 0.5 | 1.5 ± 0.4 |

TABLE 3

Biodistribution of the solution of $^{188}$Re-DTDD in lipiodol in mice

| Specimen | Time post-Injection | | | | |
|---|---|---|---|---|---|
| | 10 min<br>3 mice | 30 min<br>3 mice | 1 hr<br>4 mice | 3 hr<br>4 mice | 24 hr<br>3 mice |
| Blood | 13.0 ± 0.6 | 9.5 ± 1.1 | 7.0 ± 0.8 | 5.1 ± 1.2 | 0.6 ± 0.2 |
| Muscle | 2.4 ± 0.1 | 2.0 ± 0.2 | 1.5 ± 0.3 | 1.0 ± 0.2 | 0.3 ± 0.0 |
| Fat | 5.5 ± 0.4 | 4.4 ± 0.8 | 4.1 ± 0.6 | 2.4 ± 0.4 | 0.6 ± 0.2 |
| Heart | 9.1 ± 2.3 | 5.0 ± 0.9 | 5.5 ± 0.4 | 2.7 ± 0.7 | 1.5 ± 0.3 |
| Lung | 137.4 ± 13.1 | 85.1 ± 7.1 | 82.2 ± 15.1 | 61.9 ± 10.3 | 47.2 ± 9.2 |
| Liver | 14.9 ± 0.7 | 14.6 ± 2.2 | 13.2 ± 2.8 | 7.7 ± 0.6 | 3.3 ± 1.1 |
| Spleen | 5.6 ± 0.3 | 4.8 ± 0.4 | 3.5 ± 0.5 | 2.9 ± 0.6 | 3.3 ± 1.0 |
| Stomach | 18.3 ± 4.4 | 36.0 ± 5.9 | 49.2 ± 7.0 | 37.7 ± 12.3 | 5.4 ± 1.6 |
| Small intestine | 4.8 ± 0.3 | 8.3 ± 0.7 | 9.7 ± 1.2 | 11.6 ± 0.3 | 9.2 ± 6.9 |
| Kidney | 9.9 ± 0.7 | 7.4 ± 0.5 | 6.2 ± 0.7 | 5.2 ± 0.7 | 1.9 ± 0.3 |

TABLE 4

Biodistribution of the solution of $^{188}$Re-HTDD in lipiodol in mice

| Specimen | Time post-Injection | | | | |
|---|---|---|---|---|---|
| | 10 min<br>4 mice | 30 min<br>4 mice | 1 hr<br>3 mice | 3 hr<br>4 mice | 24 hr<br>4 mice |
| Blood | 8.1 ± 1.5 | 9.1 ± 5.3 | 4.2 ± 0.5 | 2.8 ± 0.5 | 0.6 ± 0.1 |
| Muscle | 1.9 ± 0.3 | 1.5 ± 0.2 | 1.1 ± 0.2 | 0.8 ± 0.2 | 0.4 ± 0.1 |
| Fat | 3.9 ± 1.5 | 2.8 ± 0.5 | 2.7 ± 0.6 | 2.0 ± 0.6 | 0.8 ± 0.3 |
| Heart | 9.4 ± 3.0 | 6.0 ± 1.1 | 4.7 ± 0.9 | 4.5 ± 0.8 | 2.2 ± 0.8 |
| Lung | 211.3 ± 30.0 | 185.6 ± 20.9 | 177.8 ± 18.4 | 157.3 ± 28.6 | 118.0 ± 19.5 |
| Liver | 11.6 ± 1.7 | 15.9 ± 1.6 | 14.4 ± 2.5 | 9.0 ± 1.8 | 5.6 ± 1.0 |
| Spleen | 3.6 ± 0.8 | 3.1 ± 0.2 | 3.0 ± 0.8 | 2.7 ± 0.1 | 9.3 ± 5.2 |
| Stomach | 7.4 ± 1.6 | 15.1 ± 2.9 | 21.0 ± 1.7 | 19.3 ± 4.0 | 5.5 ± 1.7 |
| Small intestine | 3.4 ± 0.5 | 6.5 ± 0.6 | 9.3 ± 1.0 | 12.2 ± 1.3 | 6.2 ± 3.4 |
| Kidney | 7.0 ± 1.8 | 6.5 ± 0.9 | 6.1 ± 1.4 | 6.2 ± 1.2 | 3.3 ± 0.7 |

INDUSTRIAL APPLICABILITY

As apparent from the above description, the present invention provides novel diaminedithiol derivatives or pharmaceutically acceptable salts thereof, and radiorhenium or radiotechnetium complex thereof. The present invention also provides a composition for treating liver cancer comprising a complex of diaminedithiol derivative-radiorhenium, which can be prepared easily and is stable after preparation, characterized by its high rate of accumulation and retention in liver cancer tissue, thereby being capable of achieving an efficient treatment of liver cancer without any side effects.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A diaminedithiol derivative of Formula 2 or a pharmaceutically acceptable salt thereof:

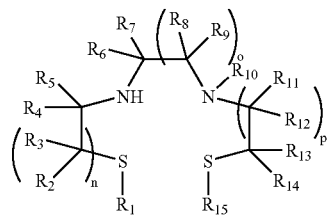

2 wherein:

$R_2$, $R_3$, $R_8$ to $R_{14}$ are independently hydrogen or lower alkyl having $C_1$ to $C_5$; $R_4$ and $R_5$ are independently hydrogen or lower alkyl having $C_1$ to $C_5$ or they form oxo (=O) group; $R_6$ and $R_7$ are independently hydrogen or lower alkyl having $C_1$ to $C_5$ or they form oxo (=O) group, in which at least one of $R_2$ to $R_{14}$ is higher alkyl having $C_{15}$ to $C_{24}$ and $R_4$ to $R_7$ don't form two oxo (=O) groups at the same time;

$R_1$ and $R_{15}$ are independently hydrogen or thiol protecting group such as benzoyl, acetamidomethyl, diphenylmethyl, ethylaminocarbonyl, t-butyl, trityl and acetyl, or $R_1$ and $R_{15}$ together form a S—S bond; and, n, o, p are independently 1 or 2.

2. The diaminedithiol derivative or a pharmaceutically acceptable salt thereof according to claim 1, wherein $R_{10}$ is higher alkyl having $C_{15}$ to $C_{24}$.

3. The diaminedithiol derivative or a pharmaceutically acceptable salt thereof according to claim 1, wherein $R_{10}$ is higher alkyl having $C_{15}$ to $C_{20}$.

4. The diaminedithiol derivative or a pharmaceutically acceptable salt thereof according to claim 2, wherein $R_{10}$ is linear alkyl without a branch.

5. The diaminedithiol derivative or a pharmaceutically acceptable salt thereof according to claim 4, wherein n, o and p are all together 1.

6. The diaminedithiol derivative or a pharmaceutically acceptable salts thereof according to claim 5, wherein $R_2$, $R_3$, $R_{13}$ and $R_{14}$ are all together methyl and $R_1$, $R_4$, $R_5$, $R_6$, $R_7$, $R_8$, $R_9$, $R_{11}$, $R_{12}$ and $R_{15}$ are all together hydrogen.

7. The diaminedithiol derivative or a pharmaceutically acceptable salts thereof according to claim 1, wherein $R_4$ and $R_5$ form oxo (=O) group.

8. The diaminedithiol derivative or a pharmaceutically acceptable salts thereof according to claim 1, wherein $R_6$ and $R_7$ form oxo (=O) group.

9. A complex of a diaminedithiol derivative according to claim 1, with radiorhenium or radiotechnetium.

10. The diaminedithiol derivative or a pharmaceutically acceptable salt thereof according to claim 3, wherein $R_{10}$ is linear alkyl without a branch.

11. The diaminedithiol derivative or a pharmaceutically acceptable salt thereof according to claim 10, wherein n, o and p are all together 1.

12. The diaminedithiol derivative or a pharmaceutically acceptable salts thereof according to claim 11, wherein $R_2$, $R_3$, $R_{13}$ and $R_{14}$ are all together methyl and $R_1$, $R_4$, $R_5$, $R_6$, $R_7$, $R_8$, $R_9$, $R_{11}$, $R_{12}$ and $R_{15}$ are all together hydrogen.

13. A composition for treating liver cancer comprising a complex of a diaminedithiol derivative of claim 9 as an active ingredient in a therapeutically effective amount.

* * * * *